US007869031B2

(12) United States Patent
Lewis et al.

(10) Patent No.: US 7,869,031 B2
(45) Date of Patent: Jan. 11, 2011

(54) DETECTION OF LATENT PRINTS BY RAMAN IMAGING

(75) Inventors: Linda Anne Lewis, Andersonville, TN (US); Raynella Magdalene Connatser, Knoxville, TN (US); Samuel Arthur Lewis, Sr., Andersonville, TN (US)

(73) Assignee: Ut-Battelle, LLC, Oak Ridge, TN (US)

( * ) Notice: Subject to any disclaimer, the term of this patent is extended or adjusted under 35 U.S.C. 154(b) by 347 days.

(21) Appl. No.: 12/180,157

(22) Filed: Jul. 25, 2008

(65) Prior Publication Data

US 2010/0021023 A1    Jan. 28, 2010

(51) Int. Cl.
*G01J 3/44* (2006.01)
(52) U.S. Cl. ....................................... 356/301
(58) Field of Classification Search ........................ None
See application file for complete search history.

(56) References Cited

U.S. PATENT DOCUMENTS

| 4,674,878 A | 6/1987 | Vo-Dinh |
| 5,017,007 A | 5/1991 | Milne et al. |
| 6,485,981 B1 | 11/2002 | Fernandez |
| 7,391,511 B1 | 6/2008 | Bratkovski et al. |
| 7,623,908 B2 * | 11/2009 | Boppart et al. ............... 600/477 |
| 2009/0103091 A1 * | 4/2009 | Jones et al. .................. 356/342 |

OTHER PUBLICATIONS

Day J.S. et al., "The Detection of Drugs of Abuse in Fingerprints Using Raman Spectroscopy I: Latent Fingerprints", *Spectrochimica Acta Part A 60*:563-568 (2004).
Osborn E.C., "Measurement of Chenodeoxycholic Acid and Deoxycholic Acid or Their Derivatives in a Mixture" *Nature 205*:284-285 (1965).
Prokes S.M. et al., "Enhanced Plasmon Coupling in Crossed Dielectric/Metal Nanowire Composite Geometries and Applications to Surface-Enhanced Raman Spectroscopy", *Applied Physics Letters 90*:093105-093105-3 (2007).
"New 'Weapon' in Forensics: Device Detects Latent Prints on Human Skin", *ScienceDaily* (3 pages) (May 3, 2008).

* cited by examiner

*Primary Examiner*—Tu T Nguyen
(74) *Attorney, Agent, or Firm*—Scully, Scott, Murphy & Presser, P.C.

(57) ABSTRACT

The present invention relates to a method for detecting a print on a surface, the method comprising: (a) contacting the print with a Raman surface-enhancing agent to produce a Raman-enhanced print; and (b) detecting the Raman-enhanced print using a Raman spectroscopic method. The invention is particularly directed to the imaging of latent fingerprints.

35 Claims, 9 Drawing Sheets

Sebaceous fingerprint on aluminum foil, brightfield image on left; Raman image on right.

Figure 9: Sebaceous fingerprint on aluminum foil, brightfield image on left; Raman image on right.

DETECTION OF LATENT PRINTS BY RAMAN IMAGING

This invention was made with government support under Contract Number DE-AC05-00OR22725 between the United States Department of Energy and UT-Battelle, LLC. The U.S. government has certain rights in this invention.

FIELD OF THE INVENTION

The present invention relates to the chemical detection and macrostructural elucidation of surface residues, and more particularly, to the forensic detection and analysis of fingerprints.

BACKGROUND OF THE INVENTION

The forensic detection and analysis of surface residues is one of the most important tools used by forensic experts for gathering evidence in crime scene investigations. For linking one or more suspects to a crime scene, fingerprint analysis of the crime scene is of particular importance in such investigations.

Fingerprints found on surfaces can be categorized according to three main types: patent (visible), plastic, and latent. Patent fingerprints result from the transfer of a visible material (e.g., paint, ink, blood, etc.) from the surface of a finger to another surface. The transferred material renders a patent fingerprint readily viewable without the use of imaging enhancement techniques. A plastic fingerprint is a fingerprint impression made in a deformable material, such as wax, soap, or putty. As used herein, a latent fingerprint is one which is not readily visible to the naked eye. Since latent fingerprints are not visible to the naked eye, an imaging enhancement technique is required to make them viewable.

The latent fingerprint is formed mainly by secretions emitted from the fingers, i.e., from sweat, and typically some portion of dirt, microorganisms, and oils. The secretion can be classified as either eccrine (i.e., "clean" and low in oils) or sebaceous (i.e., "dirty" and copious in oils).

The imaging (i.e., detection) of latent fingerprints remains among the most challenging. This is particularly so for the reason that a latent fingerprint can only become visible by application of an imaging enhancement technique. However, during the time period between when the latent fingerprint was originally deposited (i.e., as a fresh latent fingerprint) and the time of imaging, the latent fingerprint often has ample time to decompose. There are several modes of decomposition, all of which work to obscure the fingerprint and make it more difficult for imaging techniques to elucidate the fingerprint. The time period for significant amounts of decomposition to take place may in some cases be only a few hours. Some modes of decomposition include thermal, photonic, and chemical degradative processes. For example, fingerprints deposited on many surfaces often go undetected once the latent prints age over a few hours, especially when exposed to UV radiation (e.g., from sunlight or fluorescent lighting).

There are several other factors that can make the process of imaging latent fingerprints even more challenging. For example, the imageability of latent fingerprints by current techniques is very much dependent upon the surface on which the fingerprint is found. In particular, using current techniques, latent fingerprints on skin (e.g., on a corpse) are particularly difficult, if not impossible in most cases, to discern. Surfaces containing iron (III), such as steel, also rapidly decompose latent fingerprints. In addition, latent fingerprints differ in their imageability based on their chemical composition (e.g., eccrine or sebaceous). Eccrine prints, as found more predominantly from children (particularly pre-pubescent), are generally more difficult to image.

Numerous techniques are known for the detection or analysis of latent fingerprints. For example, silver nitrate has been used to develop latent fingerprints by its reaction with salts contained in the fingerprint and subsequent exposure to an actinic light source. However, exposure of the fingerprint to moisture severely limits utility of this method.

The ninhydrin technique makes use of the reaction between amino acids found in a fingerprint with triketohydrinden hydrate to form a visible fingerprint image. However, it is well known that not all fingerprints contain a suitable level of amino acids to make the ninhydrin technique generally effective.

The fingerprint dusting method involves depositing a visible powder on a surface suspected of containing latent prints. The powder adheres to oils in the print to make the print visible. However, latent prints that are not oily are generally not amenable to this method. In addition, the efficacy of the technique is very dependent on the technical proficiency of the operator.

In the iodine technique, iodine crystals are warmed in the vicinity of a surface suspected of containing latent prints. The resulting iodine vapor reacts with lipids in the latent print which causes the print to become visible. Similarly to the powder method, the iodine method is generally useful only for oily prints. In addition, the deposited iodine quickly fades over time to eventually leave the original invisible print. The iodine is also strongly oxidizing, which can cause damage to the surface or adversely alter the residue.

In the fluorogenic visualization of latent prints, the latent print is treated with one or more chemical reagents (e.g., a luminescent dye) that react with compounds in the print to form a fluorescent product. However, the number of active compounds in the print capable of forming a fluorescent product are limited. For example, the technique typically relies on the fingerprint containing certain amino acids.

In the cyanoacrylate (superglue) fuming technique, cyanoacrylate monomer (e.g., as obtained by heating a superglue composition) reacts with a one or more water-soluble components to cause polymerization of the monomer. Some of the water-soluble components that may initiate polymerization include, for example, sodium lactate, inorganic salts, free amino acids, urea, mucoproteins, and ammonia. Sebaceous components are generally inert in the initiation process, but can act to solubilize and accumulate the monomer for subsequent polymerization. In order for the cyanoacrylate method to work, the print needs to be hydrated. However, unlike oily prints, clean (eccrine) prints do not contain hygroscopic materials such as di- and mono-acyl glycerols and glycerol. As a result, clean prints are not able to maintain a hydrated print composition, and thus, become dehydrated within relatively short time frames to an extent that the superglue fuming technique is no longer effective. For example, clean prints that are older than 48 hours prior to fuming are typically so severely degraded that the superglue fuming technique is no longer useful. Attempts at simple rehydration of the prints have generally not been successful. Furthermore, latent fingerprints lose cyanoacrylate initiator (particularly lactate) via photodegradation. Therefore, latent fingerprints that have undergone photodegradation are also difficult if not impossible to image using the superglue fuming method.

Optical vibrational spectroscopic imaging work has been conducted on latent fingerprints using Fourier transform infrared (FTIR) spectroscopy. However, the FTIR technique generally suffers from a high amount of interference from water background signals. In addition, the FTIR technique is mainly applicable to oily prints, and is significantly limited when applied to clean prints. The FTIR technique is also limited in its effectiveness for imaging decomposed latent prints and latent prints residing on difficult surfaces, such as skin.

As shown, there remains a need in the art for an effective and reliable method for the imaging of a wide range of latent fingerprints under a variety of conditions. There is a particular need for a method capable of imaging latent fingerprints that are traditionally difficult or impossible to image using methods known in the art, particularly latent fingerprints that have undergone decomposition or that reside on difficult surfaces, such as skin, steel, and rough or porous surfaces. There is an additional need in the art for a method which, during the course of imaging a fingerprint or other type of print, is capable of detecting or identifying one or more chemical species of interest in the fingerprint or other print.

SUMMARY OF THE INVENTION

These and other objectives, as will be apparent to those having ordinary skill in the art, have been achieved by providing an improved method for detecting a print (e.g., a fingerprint) by the application of a Raman spectroscopic technique on the print. In a preferred embodiment, a latent print (i.e., a surface suspected of containing a latent print) is analyzed by a surface-enhanced Raman spectroscopic (SERS) technique. The SERS method preferably involves first contacting the print with a Raman surface-enhancing agent to produce a Raman-enhanced print. The Raman-enhanced print is then analyzed by a Raman spectroscopic technique to image and/or further analyze the print.

The method, as will be described in more detail below, is advantageously non-destructive and capable of imaging a wide variety of latent fingerprints under numerous conditions, including fingerprints residing on obscuring surfaces, such as skin, steel, and rough or porous surfaces. The method is also advantageously capable of imaging traditionally difficult types of latent fingerprints, such as clean (eccrine), children's (particularly pre-pubescent), and decomposed fingerprints. The method is also capable of detecting or identifying one or more chemical species of interest, such as drug, firearm, or explosive chemicals, that may be present in the fingerprint or other print.

DETAILED DESCRIPTION OF THE INVENTION

Figure 1:
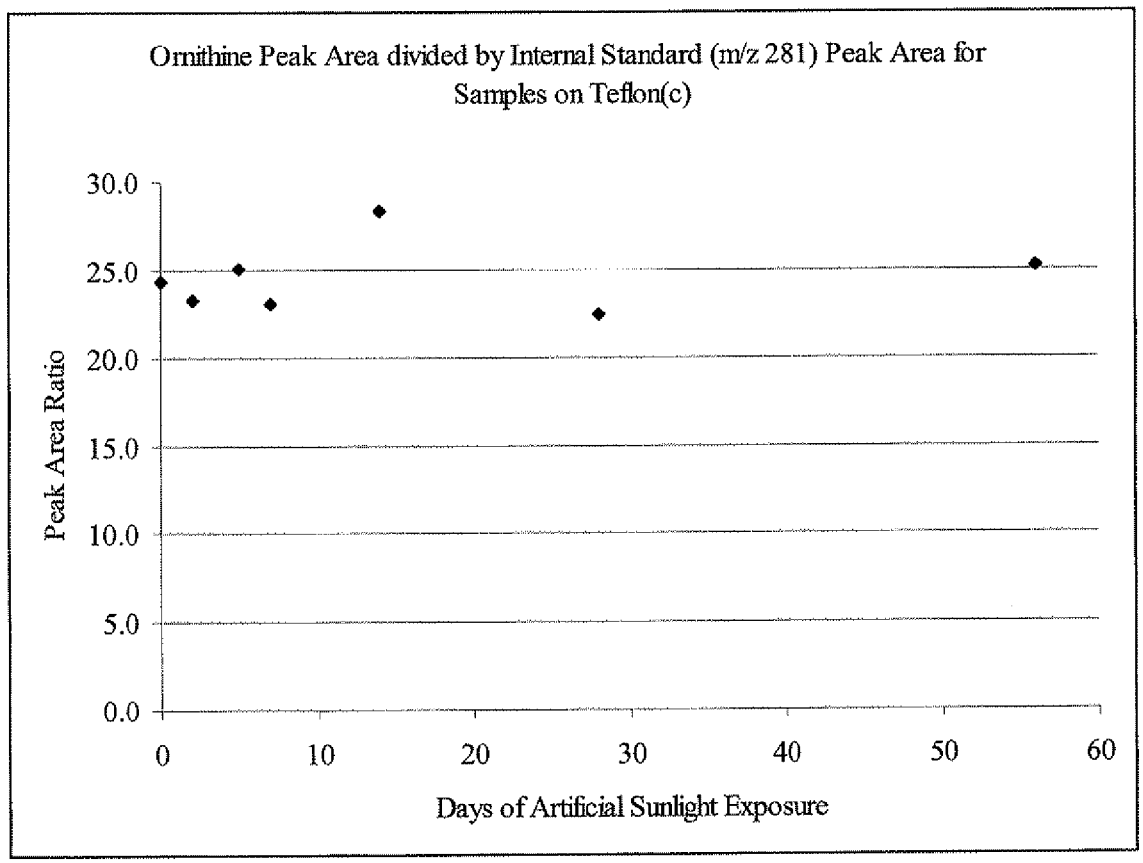
FIG. 1 Peak area ratio data for photodegradation experiments of ornithine on Teflon FIG. 2 Peak area ratio data for photodegradation experiments of glycine on steel FIG. 3 Comparison of Raman spectra of an oily fingerprint with and without silver colloid treatment.

The present invention is directed to a method for detecting a print (i.e., imprint) on a surface. The term "detecting" as used herein refers primarily to the imaging of the print to elucidate (i.e., make visible), for example, the macrostructural features (e.g., overall shape and/or patterns) of the print. A pattern can include any of the surface structural details of the object that made the print on the surface (hereinafter referred to as the donating object). The surface structural details include, for example, the full or partial outline of the donating object, and/or surface features, such as raised portions (e.g., ridges), recessed portions, protruding portions, unique markers, or identifiers, and the like. The term "detecting" can also mean (solely or in addition to imaging) the identification of one or more chemicals in the print.

Typically, detection of the print results from correlating one or more Raman spectral signals emanating from the print (typically, a Raman-enhanced print) with one or more chemical components of the print. Imaging of the print further involves determining the distribution of the correlated Raman spectral signals over the surface containing the print (e.g., by surface scanning or rastering).

The print can contain any residual (i.e., typically trace) chemicals inadvertently deposited on a surface by contact of the surface with another surface that donates chemicals originally residing thereon. The surface from which the chemicals originated is referred to herein as the "donating surface." The surface upon which the print is formed is referred to herein as the "receiving surface." The donating surface can belong to any inanimate object or living creature, and typically forms a print of the features of the donating surface on the receiving surface upon contact of the surfaces, by transfer of chemicals from the donating surface to the receiving surface. Some examples of inanimate donating objects and prints resulting therefrom include drinking and eating utensils (e.g., spoon, fork, knife, plate, or cup), weapons (e.g., knife or firearm), articles of clothing (e.g., glove, shoe, shirt sleeve, or hat), and articles of general use (e.g., paint brush, rope, scissors, writing utensils, and so on). The animate-derived print can result from any part of any living creature. Some examples of living creatures include humans and pets (e.g., cats, dogs, hamsters, monkeys, snakes, and so on). More typically, the animate-derived print results from a part of a human being. The human-derived prints of particular focus herein are prints caused by the hands (e.g., palm) and fingers, and more particularly, the fingers. However, the method described herein can be equally effective in the elucidation and analysis of prints of any other part of the body, e.g., foot and toe prints, and, for example, prints of the arms, legs, or face.

The surface on which a print (typically, a latent print) is suspected of residing (i.e., "the surface") can be any solid surface. Some examples of such surfaces include glass, metals, plastics, wood, paper, polymers (e.g., polymeric coats, such as a protective coating, finish, or gloss), dried paint, fabrics, natural objects (e.g., a rock or leaf), and skin. Unlike most of the methods known in the art of latent fingerprint imaging, the imaging method of the invention is highly effective on surfaces that are traditionally difficult substrates from which to image latent fingerprints. These types of surfaces are referred to herein as "difficult surfaces". Some examples of difficult surfaces include skin (e.g., from a cadaver), iron (III)-containing surfaces (e.g., steel), porous surfaces (e.g., paper, cardboard, wood, and fabrics), and rough surfaces (e.g., anodized aluminum, textured paint or walls, etched glass, and concrete).

The method of the invention utilizes a Raman spectroscopic method for analysis of the surface suspected of containing a print. As known in the art, Raman spectroscopy involves shining light (typically laser light) of a particular wavelength onto a surface and measuring the wavelengths and intensities of inelastically scattered photons. Each compound possesses a unique Raman spectral signature (i.e., chemical signature). Generally, the spectral signatures of interest are within the range of about 400-2200 $cm^{-1}$. The unique spectral signatures of different compounds is used by the current method for distinguishing spectral signatures indicative of the print from spectral signatures indicative of surface portions not containing the print. By doing so, along with suitable surface rastering or scanning techniques known in the art, an image can be developed that reflects the distribution on the surface of each type of chemical associated with each spectral signature. Accordingly, since the chemicals within a print (e.g., secreted chemicals of a finger) are different in nature than the chemical construction of the surface, imaging of the print (e.g., latent fingerprint) is now possible.

The Raman spectral signatures of numerous chemicals are known. These are referred to herein as the "spectral standards." If a Raman spectral signature for a particular chemical is not known, the spectral standard can be obtained by use of Raman spectroscopy on the pure chemical if the pure chemical is available. The source of a spectral signature can be identified by comparing the spectral signature with the spectral standards. For example, fingerprints are known to contain several types of natural components, including, for example, a variety of amino acids, urea, carboxylic acids, and the like. These components are some of the common natural components found in finger excretions (i.e., sweat of the fingers). These chemicals are specific for fingerprints because most surfaces do not contain these types of chemicals, particularly not in the appreciable amounts or combinations found in fingerprints. Accordingly, a spectral signature indicating the presence of amino acids or carboxylic acids is typically indicative of a latent fingerprint. A latent fingerprint pattern can be elucidated since a fingerprint is caused by contact with the surface by the ridges (raised portions of skin) of the finger which contain the pattern. The non-ridge portions of the finger do not contact the surface, and thus, the non-ridge portions on the surface only exhibit spectral signatures due to the surface. By scanning the surface, a distribution of the amino acids or carboxylic acids or other fingerprint-related chemicals can be found on the surface, from which an image of the latent fingerprint can be elucidated.

A latent fingerprint can be imaged by observation of one or more spectral signatures indicative of one or more chemicals known to be generally associated with fingerprints. Some chemicals generally associated with fingerprints include amino acids (e.g., leucine, isoleucine, glutamic acid, histidine, threonine, ornithine, tyrosine, aspartic acid, serine, alanine, valine, proline, and glycine), sugars (e.g., glucose), breakdown products or metabolites (e.g., urocanic acid, creatinine, uric acid, and urea), and carboxylic acids (e.g., propionic acid, lactic acid, isovaleric acid, n-hexanoic acid, acetic acid, isobutyric acid, pyruvic acid, and n-butyric acid). The presence of amino acids are particularly indicative of fingerprints. See, for example, Hamilton, P. B., "Amino-acids on hands," *Nature*, 205: 284-85 (1965), which is herein incorporated by reference. Any one or combination of these classes of chemicals, or one or more individual chemicals, can be used to identify and image latent fingerprint regions residing on a surface.

Table 1 below shows Raman spectral data for numerous fingerprint components. Each of these can be used to identify and image latent fingerprint regions.

TABLE 1

Raman spectral data for several fingerprint components

| Fingerprint Component | Vibrational Bands ($cm^{-1}$) | Active Functional Group |
|---|---|---|
| Leucine | 451-678, ~1450 | Amine |
| Glucose | 1223-1416, 1472-1667, 2078-2142 | Carbonyl |
| Glutamic Acid | 1577-1612 | Carboxylic acid, amine |
| Histidine | 550, 1481-1542, 1577-1612 | Amine, amide, carboxylic acid |
| Threonine | 450-720 | Amine |
| Ornithine | 1407-1469, 1504-1551 | Carbonyl |
| Urocanic Acid | ~1250, 1308-1374, 1608-1673 | Carboxylic acid, amine, vinyl |
| Creatinine | 550, 1229-1632 | Amine |
| Tyrosine | 875, 1445-1598 | Benzene ring stretching, Amine |
| Uric Acid | 1427-1664 | Carboxylic acid, amine (double) |
| Urea | 451-769, 1100 | Hydrocarbon, carboxylic acid |
| Propionic Acid | 800, 2275 | Hydrocarbon, carboxylic acid |
| Isovaleric Acid | 1100 | Hydrocarbon, carboxylic acid |
| n-Hexanoic Acid | 800, 900, 1200, 1375, 1625 | Hydrocarbon, carboxylic acid |
| Isobutyric Acid | 800, 1100 | Hydrocarbon, carboxylic acid |
| Acetic Acid | 800, 1100 | Hydrocarbon, carboxylic acid |
| n-Butyric Acid | 800, 1100 | Hydrocarbon, carboxylic acid |
| Aspartic Acid | ~1475-1580 | Carboxylic acid |
| Serine | 550 | Amine |
| Pyruvic Acid | ~1475-1580 | Carboxylic acid |
| Lactic Acid | ~1475-1580 | Carboxylic acid |
| Isoleucine | 451-575, 1450 | Amine |
| Glycine | 1670 | Amide |

The method described herein is effective even when the latent fingerprint has degraded (i.e., decomposed) to an appreciable extent. In one embodiment, the invention accomplishes this by identifying one or more degradation (i.e., decomposition) products, finding the unique Raman spectral signature of the one or more degradation products (whether from the literature or by experiment) to establish one or more spectral standards of degradation products, and then comparing spectral signatures obtained from a surface suspected of containing a latent print with the spectral standards of degradation products. For example, lactic acid undergoes oxidative dehydrogenation to pyruvic acid. Therefore, in acquiring spectral data from a surface, pyruvic acid can also be sought if lactic acid is not found, particularly when such degradation is suspected.

Preferably, the Raman spectroscopic technique utilized in the method described herein is a surface-enhanced Raman spectroscopic (SERS) technique. As known in the art, Raman spectral signals are generally very weak. A significant improvement in the signal intensity (e.g., by factors of $10^3$ to $10^8$) can be realized by the application of Raman surface-enhancing agents (hereinafter also referred to as "surface-enhancing agents" or "Raman enhancing agents"). For this reason, the method described herein preferably includes contact of the print with a surface-enhancing agent before the surface is studied with the Raman spectroscopic technique. Contacting the print with the surface-enhancing agent results in a Raman-enhanced print residing on the surface. The Raman-enhanced print thus contains components of the print in physical association with the surface-enhancing agent. For example, when the surface-enhancing agents are nanoparticles or nanowires, the Raman-enhanced print contains the print in contact with numerous nanoparticles or nanowires across a major portion or full extent of the print.

The surface-enhancing agent can have any of the compositions known in the art capable of enhancing Raman spectral signals. In one embodiment, the surface-enhancing agent includes one or more zerovalent noble metals. As generally known in the art, and as used herein, a "noble metal" refers to any of the metals designated as Group 9 (cobalt group) through Group 12 (zinc group) of the Periodic Table of the Elements (hereinafter, the "Periodic Table"). The Group 11 metals (i.e., copper, silver, and gold) are generally preferred noble metals for the purposes described herein. Silver (Ag) is particularly preferred. Platinum (Pt) and tungsten (W) are other useful metals for this purpose. In another embodiment, the surface-enhancing agent includes one or more transition metal oxides. The transition metal oxides referred to herein refer generally to the oxides of metals designated as Groups 3-12 (i.e., scandium through zinc) of the Periodic Table. More preferably, the transition metal oxides refer to oxides of the early transition metals, e.g., oxides of Groups 1-4 of the Periodic Table. Even more preferably, the transition metal oxides refer to oxides of Group 2 (e.g., oxides of titanium, zirconium, or hafnium). In a preferred embodiment, the transition metal oxide is titanium oxide. In yet another embodiment, the surface-enhancing agent is a semiconductor type of material (e.g., GaAs or InP).

The surface-enhancing agent can be of any suitable shape and size. However, surface-enhancing agents having edges, points, or other boundaries, are generally more effective than those having a smooth or featureless morphology. For this reason, particles of different sizes, from macroscopic to microscopic in size, have been found to be particularly effective. Nanoparticles of any of the above compositions are particularly preferred as surface-enhancing agents. When nanoparticles are used as surface-enhancing agents, the SERS technique can be more particularly referred to herein as nano-enhanced Raman spectroscopy (NERS). However, it is understood that SERS refers to any type of surface enhanced Raman spectroscopy, including NERS. NERS is capable in many instances of intensifying Raman signals by a factor in the range of $10^{10}$ to $10^{16}$.

As used herein, a nanoparticle typically refers to any particle having at least one of its dimensions less than 1 micron (1 μm), i.e., in the nanometer (nm) range. In different embodiments, the nanoparticle can have a maximum dimension of, for example, 500 nm, or 400 nm, 300 nm, 200 nm, 100 nm, 50 nm, 40 nm, 30 nm, 20 nm, 10 nm, 5 nm, 4 nm, 3 nm, or 2 nm. It is known in the art that signal enhancement is very much dependent on the size and shape of the particle. Because of this, a particle's size and shape may need to be carefully selected, or optimized or adjusted (i.e., tuned), in order to find an optimal surface enhancer for a particular sample. The optimal choice of the surface enhancer is often dependent on several factors, including, for example, the type of fingerprint (e.g., eccrine vs. sebaceous), the surface composition, and the type and level of degradation of the print.

The nanoparticles can, for example, be any of the approximately spherical colloidal or surface-functionalized nanoparticles commonly known in the art. Numerous methods are known for preparing such nanoparticles, particularly those containing one or more noble metals. Some examples of general preparative methods include solution chemical reductive methods (e.g., citrate or borohydride reduction of gold and silver metal salts), ultrasonication, thermal methods, vaporization, and sol gel synthesis. The nanoparticles can have any of a variety of other shapes, such as ovoid, rectangular, cubical, prismatic, pyramidal, tubular, rod-shaped, needle-shaped, ribbon-shaped, disk-shaped, amorphous, and so on.

In a preferred embodiment, the nanoparticle contains one dimension significantly longer (e.g., by at least two times) than the other two. Such a nanoparticle can be described as elongated. Some examples of elongated nanoparticles include, for example, nanorods, nanowires, nanoneedles, nanotubes, or nanofibers. The foregoing terms can all refer to the same type of morphology, e.g., all can be described as "nanorods". An example of such a nanoparticle is one having two dimensions within about 10-80 nm and a third dimension of about 200-800 nm. As used herein, a particle having two of its dimensions less than 1 micron and one of its dimensions extending beyond 1 micron is also referred to as a nanoparticle. An example of such a nanoparticle is one having two dimensions within about 10-80 nm and a third dimension within about 1-20 μm or 1-10 μm.

In another preferred embodiment, the nanoparticle is a noble metal-coated (i.e., shell) nanoparticle. The noble metal shell nanoparticle includes a non-noble metal interior portion (typically a dielectric material) coated with a film of the zerovalent noble metal. Some examples of suitable dielectric materials include gallium oxide (e.g., $Ga_2O_3$), indium oxide, aluminum oxide, zinc oxide (ZnO), silicon oxide, tin oxide, and titanium oxide. The shell nanoparticle can be of any desired shape, including any of the shapes described above. The interior portion (i.e., the core) can be prepared by any of the methods described above or as otherwise known in the art. The film of noble metal can be applied to the core substrates by any of the methods known in the art. For example, the noble metal can be deposited by chemical reduction or a vaporization technique. Typically, the noble metal coating is from 1 to about 30 nm thick, and more typically, about 2 to about 20 nm thick.

In a particular embodiment of the above, the shell nanoparticle has an elongated morphology. For example, in different embodiments, the elongated shell nanoparticle can contain an elongated dielectric core (e.g., of $Ga_2O_3$ or ZnO) and a coating of a noble metal, such as silver or gold. In one embodiment, the diameter of the elongated dielectric core is within the range of about 30 to 100 nm or 40 to 80 nm. Particularly preferred elongated shell nanoparticles and their syntheses are disclosed in S. M. Prokes, et al., *Applied Physics Letters*, 90, 093105 (2007), the content of which is incorporated herein by reference in its entirety.

The nanoparticles can be either mainly dispersed, or alternatively, contain some degree of agglomeration. The nanoparticles may also be surface-functionalized in any suitable manner. For example, the nanoparticles may be rendered hydrophobic, hydrophilic, reactive, non-reactive, or dispersible by careful selection of surface functionalizing groups. If desired, the nanoparticles may also be made to interconnect or overlap to form a network, a pattern, or a mesh.

Any method of contacting the print with the surface-enhancing agent can be utilized in the inventive method. In one embodiment, the surface-enhancing agent is applied onto a surface suspected of containing a print (i.e., generally a latent print of any kind). In order to apply the surface-enhancing agent onto the print, the surface-enhancing agent is preferably particulate in form. The surface-enhancing particles can be applied by any of the methods capable of applying particles onto a surface, including, for example, spraying, misting, aerosolizing, nebulizing, atomizing, brushing, sprinkling, or a combination thereof, or the like.

In another embodiment, the surface-enhancing agent is contacted with the print by lifting components of the print from the native surface onto a surface containing a surface-enhancing agent (i.e., a Raman-enhancing surface). The surface-enhancing agent can be incorporated into the Raman-enhancing surface in any suitable manner. For example, the Raman-enhancing surface can be a composite or nanocomposite containing surface-enhancing nanoparticles in a solid matrix of; for example, a polyurethane. Alternatively, the Raman-enhancing surface is composed of, or contains a coating of, the surface-enhancing material. For example, the Raman-enhancing surface may be composed of, or contains a coating of; gold, silver, copper, or platinum. In a preferred embodiment, the Raman-enhancing surface is roughened. A roughened surface is generally more surface enhancing by having a higher density of edges, points, and other protrusions. A surface can be roughened by, for example, plasma treatment, an acid etch, or both. The Raman-enhancing surface can be rigid (e.g., silver particles or film on a glass slide) or flexible. Flexible Raman-enhancing surfaces are particularly convenient. Some examples of suitable flexible surfaces can be found in U.S. Pat. No. 4,674,878, the entire content of which is incorporated herein by reference.

After the surface has been treated with the surface-enhancing agent, the surface is analyzed using a Raman spectroscopic technique. Any of the Raman spectroscopic techniques known in the art capable of processing emitted spectral signals over a surface is suitable for the method described herein. The technique typically utilizes a focused and intense monochromatic light beam to impinge on the surface of interest. The incident (impinging) light source is typically a laser. The light source can be within any of the suitable wavelengths of light, such as, for example, the visible, near infrared (nIR), infrared, or near ultraviolet wavelengths. Inelastically scattered photons (i.e., the emitted spectral signals) from the surface are then analyzed according to their wavelengths and intensities. The Raman technique can also make use of polarized light, as in polarized Raman spectroscopy.

The Raman technique can image the surface in any suitable manner. For example, in direct imaging, the surface is scanned for spectral signals over a short range of wavenumbers in search of one or more types of chemicals. In hyperspectral imaging (or "chemical imaging") a wide range of spectral signals are scanned over the surface such that images can be generated showing the distribution and amounts of different chemicals over the surface. Other applicable types of Raman spectroscopy include resonance Raman spectroscopy, stimulated Raman spectroscopy, spatially offset Raman spectroscopy (SORS), and coherent anti-Stokes Raman spectroscopy (CARS). The Raman technique can also incorporate methods for negating background signals, such as those commonly found for water and metal surfaces.

In a particular embodiment, time-resolved Raman spectroscopy is used. The time resolution can be accomplished by, for example, switching on an imaging (e.g., ICCD) camera for a specified time microseconds after the firing of a pulsed laser. In this manner, any light attributable to long-lived fluorescence is minimized. In addition, the contribution from ambient light is reduced by this variation.

In a preferred embodiment, chemical imaging is acquired by expanding the impinging laser light by 20 mm in diameter, collecting the light over a narrow wavelength range defined by the tunable filter, and an image at essentially a single wavelength of Raman scattered light is created and stored. The tunable filter then switches to another wavelength and the process is repeated. Each successive Raman wavenumber image is stacked on top of the last until a hyperspectral cube is created wherein the X and Y axes define an intensity map of the sample at a near-single wavenumber electromagnetic region and the Z direction illustrates the Raman spectrum from single spots once the cube is constructed via tuning across whatever wavenumber regions are defined by experimental parameters. The difference in this type of imaging as contrasted with conventional Raman rastering or mapping is the higher speed with which the image can be collected. The higher speed is particularly beneficial in a situation where the target analyte is known, thus allowing for a predetermined spectral region to be targeted by the tunable filter. Conventional rastering or mapping creates a Raman image by collecting an entire Raman spectrum at each of many spots across the sample, after which the intensity map is reconstructed by following defined wavenumber regions within the X-Y grid of whole spectra. This approach is more suitable for gaining descriptive information from maps of unknown substances as it is more time consuming than large field of view imaging using known wavenumber regions of interest for analytes, such as fingerprint components.

In a preferred embodiment, the method utilizes a portable Raman spectroscopic system. Preferably, the system is compact and lightweight (e.g., 5-10 cu. ft. and less than 40 lbs.). Typical power requirements are 90-260 VAC and less than 1,000 W. The camera preferably contains a back illuminated and thermoelectrically (TE) cooled CCD with, for example, 512×512 imaging, 24 micron pixels, and a 16 bit readout. The TE cooling is preferably less than −40° C. (e.g., liquid nitrogen-cooled). The required laser wavelength and power is dependent on the type of print (e.g., chemical make up), but is typically in the range of 500 to 800 nm in wavelength and 100 to 500 mW in power. For example, the laser can be a 632.8 nm helium-neon laser. A tunable filter is preferably employed. The tunable filter is preferably a liquid crystal (i.e., liquid crystal tunable filter, or LCTF) capable of 500-750 nm or 650-1,150 nm tunability and a typical bandpass of about 0.25 nm. A macro zoom lens is also preferably employed. The macro zoom lens is preferably capable of a 7:1 zoom range, a maximum field of view of about 20-30 mm, and a magnification range of about 0.38-2.6×. The macro zoom lens can preferably operate by visible or nIR wavelengths. A laser rejection filter is also preferably employed. The laser rejection filter is preferably sharp edge and long pass and is dependent on the laser characteristics. Preferably, a computer unit is incorporated into the system for signal processing and data analysis. The computer is preferably suitable for regular transport, such as a laptop ruggedized for field operation and having a USB 2.0 interconnection. Preferably, capable software for signal processing and/or data analysis is also included. A preferred software for this purpose is ChemImage Xpert™ available from ChemImage Corp.

Using the method described above, a variety of prints, particularly fingerprints, can be conveniently imaged. The method is particularly convenient in that prints can be imaged directly on-site on native surfaces by use of the portable Raman spectroscopic system described above. However, the method can also be practiced by removing a native surface, or a portion thereof and transferring it to another location where the method is practiced. Alternatively, a suspected print can be lifted from the native surface using any of the print lifting techniques known in the art, and the lifted print analyzed according to the method described above.

In one embodiment, the analysis is used to discern macro-structural characteristics of the print, such as the patterns in a latent fingerprint. In another embodiment, the analysis is used to identify one or more chemical components of the print. For example, the method can be used to test for the presence of minute traces of certain chemicals of interest, such as a drug, explosive, or firearm residue, that may be present on a fingerprint. Some examples of drugs include illegal drugs (e.g., cocaine, heroin, marijuana, methamphetamine, LSD, and the like), as well as over-the-counter (OTC) and prescribed types of drugs (e.g., acetaminophen, pseudoephedrine, or an antibiotic). Some examples of explosive materials that can be detected include those containing nitro groups (e.g., RDX, TNT, and PETN), peroxide functionality, and the like. Some examples of firearm residues include smokeless powder (e.g., nitrocellulose), its stabilizers, and decomposition products. Numerous other types of chemicals can be sought or identified by this method, including, for example, food-related chemicals and industrial chemicals. The purpose of identifying one or more chemicals in a print is typically for the purpose of a criminal investigation, and more typically, to connect one or more suspects to a crime scene. However, it is contemplated that the technique can also be used for other purposes not connected to a criminal investigation.

Examples have been set forth below for the purpose of illustration and to describe the best mode of the invention at the present time. However, the scope of this invention is not to be in any way limited by the examples set forth herein.

EXAMPLE 1

Artificial Fingerprint Formulation

Hamilton's quantitative data of the individual amino acids plus urea found in an eccrine-only thumbprint (see Hamilton P. B. "Amino-acids on Hands" Nature, 1965; 205 (4968), 284-285) was combined with reference data from the Geigy Scientific Tables on eccrine sweat secretions (see "Sweat" Lentner C, editor; Geigy Scientific Tables. Volume I: Units of Measurement, Body Fluids, Composition of the Body, Nutrition. 8th rev. ed. West Caldwell, N.J.: Ciba-Geigy Limited, 1981; 108-112) to create a 44-component artificial eccrine fingerprint solution, as shown in Table 2 below.

TABLE 2

Artificial Eccrine Fingerprint Solution

| Components | mg/L (=µg/mL) | % Composition |
|---|---|---|
| AMINO ACIDS: | | |
| Serine | 399.21 | 7.16 |
| Glycine | 191.00 | 3.42 |
| Ornithine (as Ornithine HCl) | 205.46 | 3.68 |
| Aspartic acid | 109.71 | 1.97 |
| Histidine | 100.08 | 1.79 |
| Alanine | 92.59 | 1.66 |
| Threonine | 76.84 | 1.38 |
| Lysine | 57.63 | 1.03 |
| Valine | 54.58 | 0.98 |
| Leucine | 51.71 | 0.93 |
| Glutamic acid (as monohydrate) | 53.26 | 0.95 |
| Proline | 45.38 | 0.81 |
| Phenylalanine | 41.44 | 0.74 |
| Tyrosine | 38.96 | 0.70 |
| Isoleucine | 37.61 | 0.67 |
| Arginine | 31.21 | 0.56 |
| Citrulline | 25.11 | 0.45 |
| Methionine | 10.69 | 0.19 |
| Taurine | 4.48 | 0.08 |
| Cystine | 0.72 | 0.01 |
| α-Amino-n-butyric acid | 0.36 | 0.01 |
| FATTY ACIDS: | | |

TABLE 2-continued

Artificial Eccrine Fingerprint Solution

| Components | mg/L (=µg/mL) | % Composition |
|---|---|---|
| Acetic acid | 7.69 | 0.14 |
| Propionic acid | 0.26 | 0.005 |
| Butyric acid | 0.21 | 0.004 |
| Isovaleric acid | 0.11 | 0.002 |
| Hexanoic acid | 0.10 | 0.002 |
| Isobutyric acid | 0.07 | 0.001 |
| Urea | 1180.00 | 21.15 |
| Sodium chloride (NaCl) | 1138.46 | 20.41 |
| Potassium chloride (KCl) | 640.74 | 11.49 |
| Lactic acid | 616.00 | 11.04 |
| Ammonium hydroxide ($NH_4OH$) | 107.01 | 1.92 |
| Calcium sulfate ($CaSO_4$) | 98.50 | 1.77 |
| Glucose | 70.00 | 1.25 |
| Pyruvic acid | 40.00 | 0.72 |
| Sodium sulfate ($Na_2SO_4$) | 24.92 | 0.45 |
| Magnesium sulfate ($MgSO_4$) | 15.85 | 0.28 |
| Creatinine | 4.60 | 0.08 |
| Zinc chloride ($ZnCl_2$) | 2.40 | 0.04 |
| Uric acid | 2.02 | 0.04 |
| Sodium bicarbonate ($NaCO_3H$) | 1.45 | 0.03 |
| Acetylcholine iodide | 0.1214 | 0.00218 |
| Histamine | 0.0135 | 0.00024 |
| Sodium iodide (NaI) | 0.0045 | 0.00008 |

After screening the individual component chemicals for ease of detection by Surface Enhanced Raman Spectroscopy (SERS), the following SERS-active components were chosen for further study: aspartic acid, glutamic acid, glycine, histidine, ornithine, serine, threonine, urea, and lactic acid. Aqueous fingerprint standards were made of each amino acid at five times its single-print concentration, a mixture of all seven amino acids at five times their single-print concentrations, urea at 5 times and 250 times its single-print concentration, and lactic acid at 5 times and 100 times its single-print concentration. All amino acids (DL-aspartic acid, DL-glutamic acid monohydrate, glycine, DL-histidine, L-ornithine HCl, DL-serine, DL-threonine) and urea were purchased from Aldrich (Milwaukee, Wis.) at purity levels of greater than 98%; lactic acid (an 88% racemic mix in water) was purchased from Mallinckrodt (Phillipsburg, N.J.). To prevent bacterial growth contamination of these standards, all solutions were biologically sterilized by filtering through 0.1 µm-pore size, 32 mm-diameter acrodisc sterile syringe filters with Supor membrane (Pall Corporation, East Hills, N.Y.). The solution containers were flame sterilized. All sterilization procedures were carried out in a biological hood.

EXAMPLE 2

Photodegradation Studies of the Artificial Fingerprint Formulation

Using gas-tight syringes for precise volume control, 28 µL (equivalent to the standard volume of material in one fingerprint) of the individual 5× amino acid standards were deposited on separate sets of seven Teflon® discs (22 mm-diameter) and seven steel coupons (19.6 mm×15.8 mm×4.4 mm), for a total of 98 amino acid samples. The samples were allowed to dry overnight in the dark, before being exposed to a 200-500 Watt Xe/HgXe Arc Lamp intense light source (Oriel Corporation Model 87301, Stratford, Conn.) for periods of time equivalent to 0, 2, 5, 7, 14, 28, and 56 days. The light source emits visible, UV-A, UV-B, and UV-C wavelengths, simulating 365 days of sunlight exposure in 24 hours of lamp use. Table 3 (below) provides the lamp exposure times that correlated with the desired duration of continuous sunlight exposure. The same sample preparation procedure was repeated with the 250× Urea and 100× Lac standards, for an additional 28 samples. Teflon discs were reused throughout the study, with a multi-step cleaning with lab soap, distilled water, acetonitrile, and methanol between each use. Steel coupons were used only once.

TABLE 3

Sample Time under Xe/XeHg Lamp to Simulate
Given Amount of Sunlight Exposure

| Time under Xe/XeHg Lamp | Time Exposed to Sunlight |
|---|---|
| 0 hr 0 min 0 sec | 0 days |
| 0 hr 7 min 53 sec | 2 days |
| 0 hr 19 min 44 sec | 5 days |
| 0 hr 27 min 37 sec | 7 days |
| 0 hr 55 min 14 sec | 14 days |
| 1 hr 50 min 28 sec | 28 days |
| 3 hr 40 min 56 sec | 56 days |

EXAMPLE 3

Thermal Degradation Studies of the Artificial Fingerprint Formulation

Thin galvanized steel coupons (15.7 mm×15.7 mm×0.5 mm) were wiped with acetonitrile and methanol to remove lubrication oils used in the coupon-cutting process, sanded with 4000-grit (or better) sandpaper to remove any possible surface oxidation, and wiped again with acetonitrile and methanol. Using gas-tight syringes for precise volume control, 28 μL of the 5× standard amino acid mixture was deposited on four steel coupons. The samples were allowed to dry overnight in the dark. A commercially-available 120-V, 1200-W heat gun (Black&Decker Model No. 9756, Hunt Valley, Md.) was turned on to the "high" setting for at least three minutes. A vise-grip clamp was used to grasp a steel coupon along its edge and suspend it directly over the heat gun, with the non-deposited side facing the heat source. A thermocouple (Omega Engineering, Stamford, Conn.) in contact with the steel coupon measured the temperature experienced by the side spotted with the fingerprint sample. Once the desired temperature was achieved (50° C., 100° C., or 150° C.) the steel coupon was immediately removed from the heat source and allowed to cool on a wire rack for three minutes. The fourth coupon was not heated, to be used as the ambient reference. The thermal degradation procedure was repeated with the 250× Urea and 100× Lac standards.

EXAMPLE 4

Amino Acid Sample Analysis

The amino acid samples were placed face-down in glass vials containing 1 mL of a 50 mM aqueous solution of sodium dodecyl sulfate (Fluka, Seelze, Germany); then the vials were placed in an ultrasonic bath for 30 min to promote extraction. The solvent was recovered and taken through the "EZ:faast™ for Free Physiological Amino Acid Analysis by LC-MS" derivatization kit (Phenomenex, Torrance, Calif.). This EZ:faast™ sample derivatization consisted of the introduction of a mixture of three internal standards and a solid phase extraction utilizing amino acid-trapping sorbent particles, followed by the proprietary derivatization and a liquid/liquid extraction. The organic liquid layer was evaporated to dryness under nitrogen, then reconstituted in 100 μL of a 2:1 (v/v) mixture of 10 mM ammonium formate (Fluka, Seelze, Germany) in MeOH and 10 mM ammonium formate in $H_2O$.

Samples were analyzed by liquid chromatography coupled to positive-ion electrospray mass spectrometry using an Agilent (Wilmington, Del.) 1100 Series LC instrument and Bruker Daltonics (Billerica, Mass.) Esquire-LC MS instrument with settings as presented in Table 3 above.

EXAMPLE 5

Urea and Lactic Acid Sample Analysis

The urea and lactic acid samples were placed face-down in glass vials containing 1 mL of MeOH:$H_2O$ (1:1, v/v) with 0.15% formic acid (from Formic Acid 88%, JTBaker Inc., Phillipsburg, N.J.). The vials were placed in an ultrasonic bath for 30 minutes to promote extraction. The solvent was removed and mixed with an equal volume of internal standard. Urea samples used an internal standard of 100 ppm aqueous melamine (as Melamine 99%, Aldrich, Milwaukee, Wis.); lactic acid samples were spiked with 100 ppm aqueous cyanuric acid (Aldrich, Milwaukee, Wis.) as internal standard. The samples were filtered through 0.1 μm Supor-membrane sterilized filters (Pall Corporation, East Hills, N.Y.), then analyzed by direct infusion at 26.7 μL/min into an atmospheric pressure chemical ionization mass spectrometer (APCI-MS) using a Bruker Daltonics (Billerica, Mass.) Esquire-LC MS instrument with settings as presented in Table 4 below.

TABLE 4

Instrument Settings for MS Analysis of Urea and Lactic
Acid Photodegradation and Thermal Degradation Samples

| MASS SPECTROMETRY of UREA Samples | | | | | |
|---|---|---|---|---|---|
| Mode: | Positive-ion | | | | |
| Capillary Voltage: | −3500 V | Skim 1: | 13.0 V | Skim 2: | 8.0 V |
| End Plate Offset: | 0 V | Cap. Exit Offset: | 18.0 V | Cap. Exit: | 31.0 V |
| Corona: | 1400 V | Octopole | 2.70 V | Oct RF: | 150.0 $V_{pp}$ |
| Nebulizing Gas: | 25.0 psi $N_2$ | Octopole Δ | 2.40 V | Lens 1: | −5.6 V |
| Drying Gas: | 4.00 L/min $N_2$ | Trap Drive | 45.6 | Lens 2: | −88.0 V |
| Dry Temp: | 300° C. | | | | |
| APCI Source Temp | 325° C. | | | | |
| Target | 20,000 | | | | |
| Accumulation Time | 1.00 ms | | | | |
| Scan Range: | 50-200 m/z | | | | |

TABLE 4-continued

Instrument Settings for MS Analysis of Urea and Lactic
Acid Photodegradation and Thermal Degradation Samples

| Averages: | 100 | | | | |
|---|---|---|---|---|---|
| MASS SPECTROMETRY of LACTIC ACID Samples | | | | | |
| Mode: | Negative-ion | | | | |
| Capillary Voltage: | 0 V | Skim 1: | −13.0 V | Skim 2: | −8.0 V |
| End Plate Offset: | 0 V | Cap. Exit Offset: | −18.0 V | Cap. Exit: | −31.0 V |
| Corona: | −1700 V | Octopole | −2.70 V | Oct RF: | 150.0 $V_{pp}$ |
| Nebulizing Gas: | 25.0 psi $N_2$ | Octopole Δ | −2.40 V | Lens 1: | 5.6 V |
| Drying Gas: | 4.00 L/min $N_2$ | Trap Drive | 45.6 | Lens 2: | 88.0 V |
| Dry Temp: | 300° C. | | | | |
| APCI Source Temp | 325° C. | | | | |
| Target | 20,000 | | | | |
| Accumulation Time | 50.00 ms | | | | |
| Scan Range: | 50-200 m/z | | | | |
| Averages: | 100 | | | | |

EXAMPLE 6

Sample Extraction and Optimization

Selections on the HPLC front began with a C18 column and a trifluoracetic acid (TFA)-based mobile phase gradient. When used with an aqueous mixture of amino acids, co-elution was a major problem. References have indicated that successful separation, identification, and quantification of numerous amino acids and related molecules is possible with the C18 column using a tridecafluoroheptanoic acid (TD-FHA) mobile phase gradient. However, co-elution remained problematic during sample runs. Next, a silica column with an ACN:$H_2O$ mobile phase system was tested with the amino acids. Though separation efficiency was improved, problems remained: significant peak broadening and tailing was noted; at 40 minutes, runs were longer than desired and several amino acids were not detected (despite increased concentration levels). Finally, the EZ:faast™ free amino acid analysis kit (which utilized a Phenomenex© AAA-MS column with an $COOHNH_4$ in MeOH: $COOHNH_4$ in $H_2O$ mobile phase gradient) was tested, and resulted in appropriate resolution, sensitivity, peak shapes, and elution times for the components of the amino acid mixture. Although a method of separating and detecting the components as they existed in fingerprint material was originally sought, the success of the derivatization kit led to its adoption in this protocol.

Attention next shifted to optimizing the extraction of fingerprint material from substrates. Numerous extraction solvents/solutions (Table 5) were variously tested until a boiling 50 mM SDS aqueous solution was found to consistently extract the amino acids, even at low concentrations, for successful post-derivatization LC-MS detection. The complete sample processing and analysis protocol for the amino acid portion of eccrine fingerprints was provided in the preceding section.

TABLE 5

Solvents/Solutions Tested for Extraction of Amino Acids

| Solvent/Solution | Chosen for Extraction? |
|---|---|
| Water | no |
| Formic acid | no |
| Ethanol | no |
| Acetonitrile | no |

TABLE 5-continued

Solvents/Solutions Tested for Extraction of Amino Acids

| Solvent/Solution | Chosen for Extraction? |
|---|---|
| 0.1M Trifluoroacetic acid (aq) | no |
| 1.0M Ammonium acetate (aq) | no |
| 1.0M Ammonium acetate (aq) with 1% formic acid | no |
| 1.0M Ammonium acetate (aq) with 10% formic acid | no |
| 50 mM Sodium sodecyl sufate (aq) - boiling | yes |

In pursuit of one protocol capable of analyzing all constituents of eccrine fingerprints, the SDS extraction and EZ:faast derivatization/LC-MS analysis was attempted with the non-amino acids (i.e. urea and lactic acid). One approach involved the collection and subsequent derivatization of the wash from the solid-phase extraction step utilizing amino acid-trapping sorbent particles. However, no constituents were detected during LC-MS analysis. A second approach involved the use of specially-ordered solid-phase extraction tips designed to trap non-amino organic acids. This approach was also problematic. Therefore, instead, a separate protocol was sought for the analysis of the non-amino acid portion of eccrine fingerprints. The starting point was a DNPH derivatization followed by LC-MS analysis using a C18 column, ACN:$H_2O$ mobile phase system, and electrospray ionization MS. Although the targeted constituents were detected, reproducible quantification was difficult. A more favorable approach was chosen which utilizes an extraction solution of MeOH:$H_2O$ (1:1, v/v) with 0.15% formic acid, followed by direct infusion and APCI-MS analysis. The complete sample processing and analysis protocol for the non-amino acid portion of eccrine fingerprints was provided in the preceding section.

EXAMPLE 7

Photodegradation Studies of Amino Acids

The goal of these studies was to determine whether any of the tested amino acids experienced photo-induced degradation, and if so, to determine the rate of degradation and identify any detectable degradation products. This was accomplished by monitoring over a set of samples the relative ratio of the peak area of each amino acid to the peak area of the closest-eluting internal standard. Data processing used Bruker Daltonics software (Billerica, Mass.), and consisted of choosing the extracted ion chromatograms for the amino acid/internal standard, subtracting the baseline, 3-cycle smoothing of the chromatogram, and manually integrating the peak area. The literature accompanying the derivatization kit provided the m/z values to monitor for the amino acids and internal standards (Table 6), as well as the instructions to use the first internal standard (homoarginine, HARG) for comparison with SER, GLY, and THR and the second internal standard (methionine-d3, Met-d3) for comparison with ORN, ASP, HIS, and GLU.

TABLE 6

Basic Info on AA Ions after Derivatization Kit

| Chemical Name | Abbreviation | Reported $t_R$ (min) | AA MW (g/mol) | Derivatized AA MW + 1 (m/z) |
| --- | --- | --- | --- | --- |
| Homoarginine | HARG | 2.9 | 188.2 | 317 |
| Serine | SER | 3.7 | 105.1 | 234 |
| Glycine | GLY | 4.3 | 75.1 | 204 |
| Threonine | THR | 4.3 | 119.1 | 248 |
| Ornithine | ORN | 6.9 | 132.1 | 347 |
| Methionine-d3 | Met-d3 | 6.9 | 152.2 | 281 |
| Aspartic acid | ASP | 7.8 | 133.1 | 304 |
| Histidine | HIS | 7.8 | 155.1 | 370 |
| Glutamic acid | GLU | 8.3 | 147.1 | 318 |
| Homophenylalanine | HPHE | 12.2 | 179.2 | 308 |

Figure 2:
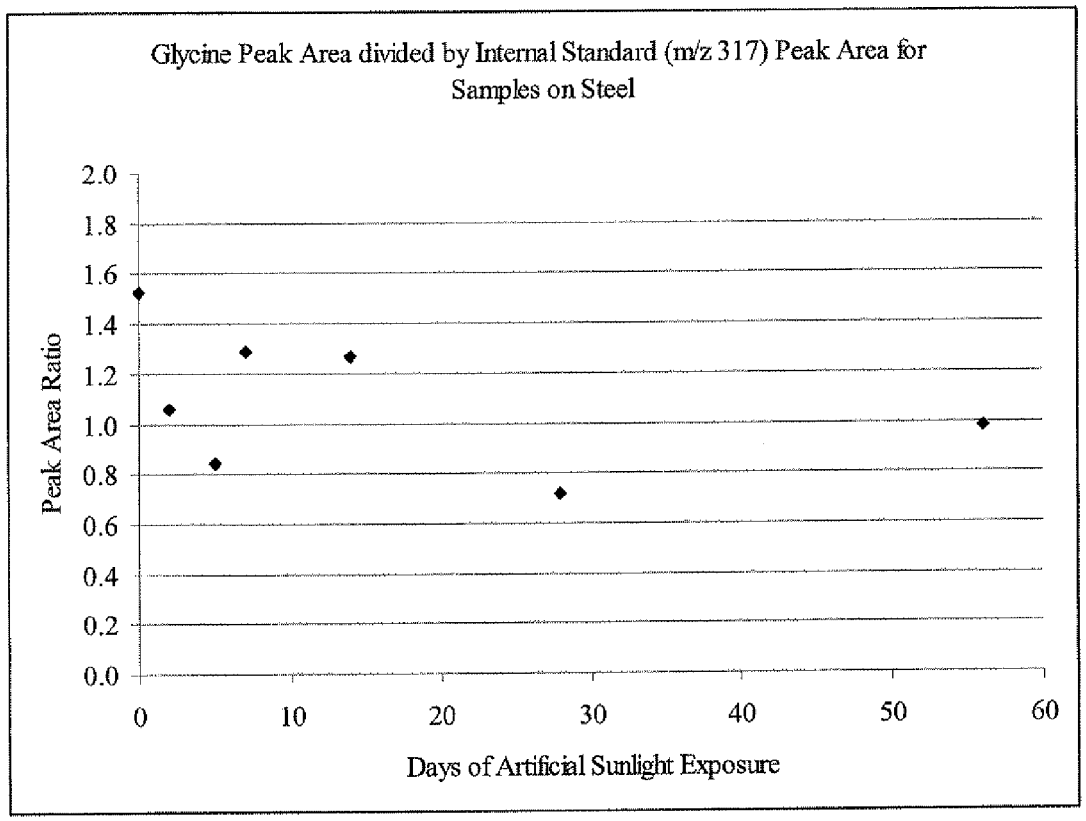

For each of the seven amino acids, the relative ratio of the amino acid peak area to the internal standard peak area remained constant across the seven timepoints within the sample set (the data for ORN on Teflon® and GLY on steel, chosen to illustrate the amino acid data sets, are provided in FIGS. 1 and 2).

EXAMPLE 8

Photodegradation Studies of Urea and Lactic Acid

The choice of extraction solvent (a formic acid-containing water:methanol mix) for the urea and lactic acid samples is compatible with direct infusion into the MS via an APCI source. Therefore, the collected data consists of spectra. However, as with the amino acid samples, peak area ratios are employed to monitor degradation. The urea samples were analyzed in positive ion mode, with urea producing an $M^+$ ion at m/z 61, and the melamine used as an internal standard producing an $M^+$ ion at m/z 127. The lactic acid samples were analyzed in negative ion mode, with lactic acid producing an $M^+$ ion at m/z 89, and the cyanuric acid used as an internal standard producing an $M^+$ ion at m/z 128.

EXAMPLE 9

Thermal Degradation Studies of Amino Acids

All seven amino acids deposited on steel were degraded to some extent in the presence of heat. Serine and glycine data yielded a large-scale reduction in detected amino acid for the sample heated to 150° C., and no peak was present for threonine at that temperature. Ornithine, aspartic acid, histidine, and glutamic acid all experienced a similar degradation pattern: there was substantial amino acid loss incurred at the 100° C. temperature point, and additional loss at the 150° C. sample. When the chromatograms were analyzed for in-growth products, none could be found.

EXAMPLE 10

Fingerprint Imaging Results from Surface Enhanced Raman Spectroscopy (SERS)

Figure 3:
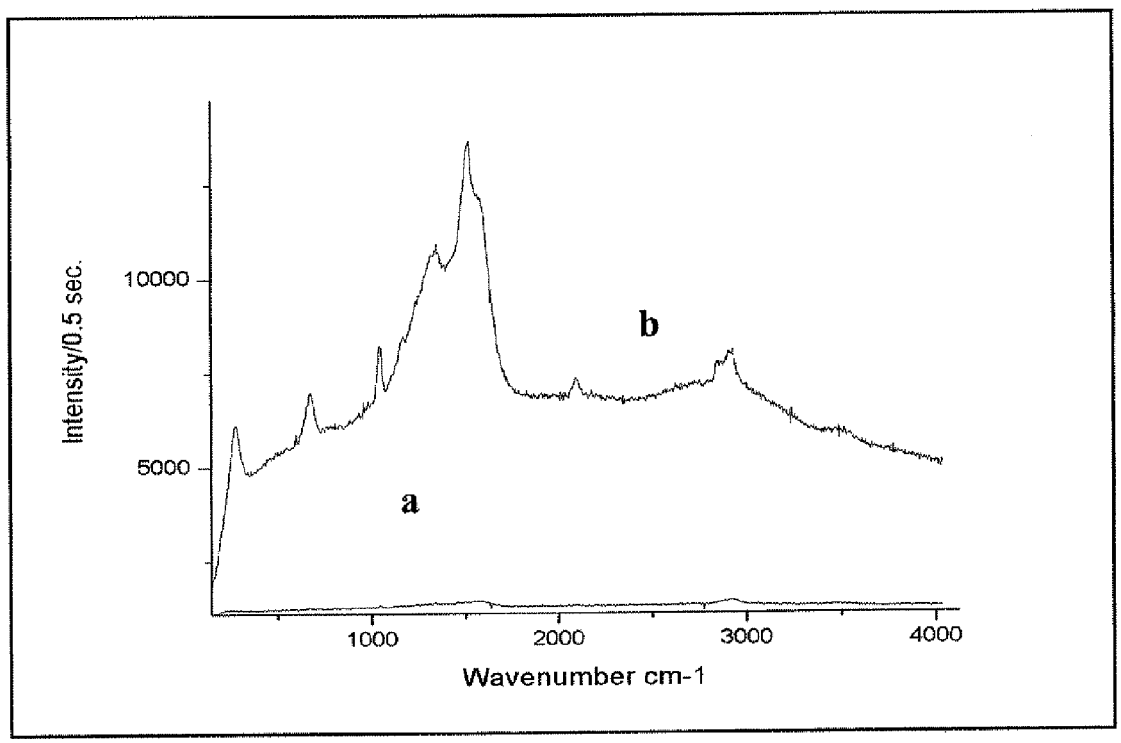

FIG. 3 shows a Raman spectra of an oily fingerprint acquired according to the method described above. The bottom spectrum (a) is for an oily fingerprint that was not treated with silver colloid while the top spectrum is for an oily fingerprint that was treated with silver colloid. The spectra acquisition conditions were 300 g/mm grating, 10 sec exposure time for untreated and 0.5 sec exposure time for treated, and laser power of 50 mW at the laser for untreated and 5 mW for treated with a 514 argon ion laser. The figure illustrates the signal enhancement gained with the use of a silver-based SERS treatment vs. non-treatment. The oily and clean fingerprints utilized in the SERS analysis above were treated by spraying a fine mist of silver colloid over each sample.

As a vibrational technique, SERS is capable of selective detection and identification on a wide range of materials, typically with sub-monolayer sensitivity. Although metal adsorption imparts some degree of selectivity for detection, SERS surfaces can be modified so that preferential adsorption of particular compounds is achieved.

Figure 4:
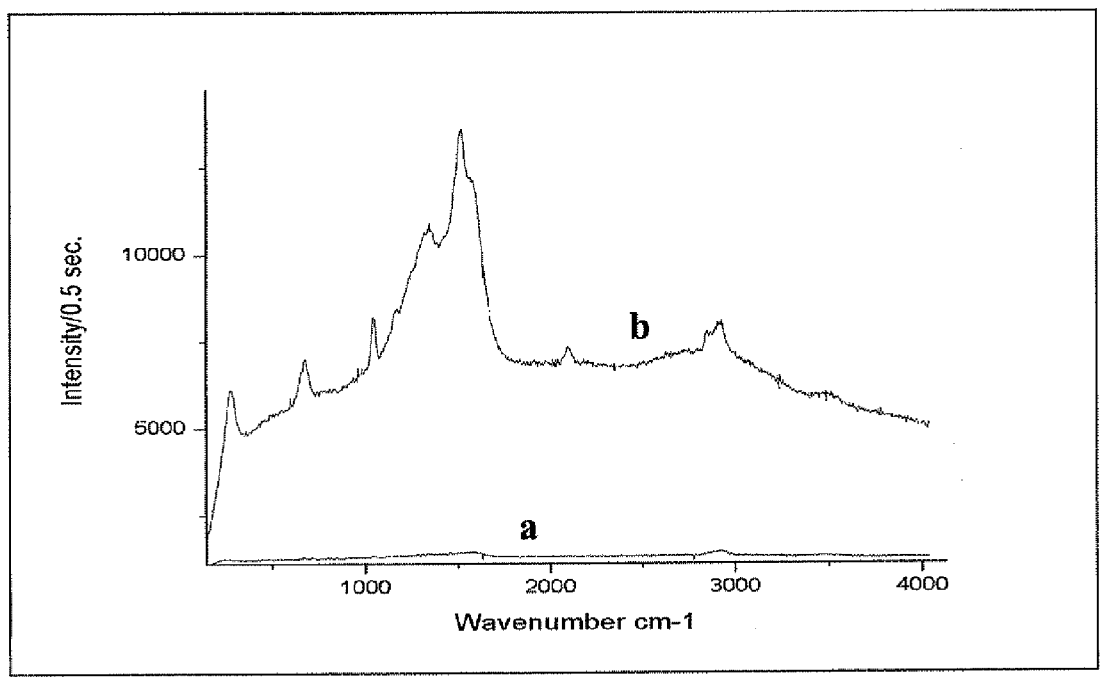
FIG. 4 Raman spectra of ridge and off-ridge portions of an oily fingerprint treated with silver colloid.
Figure 5:
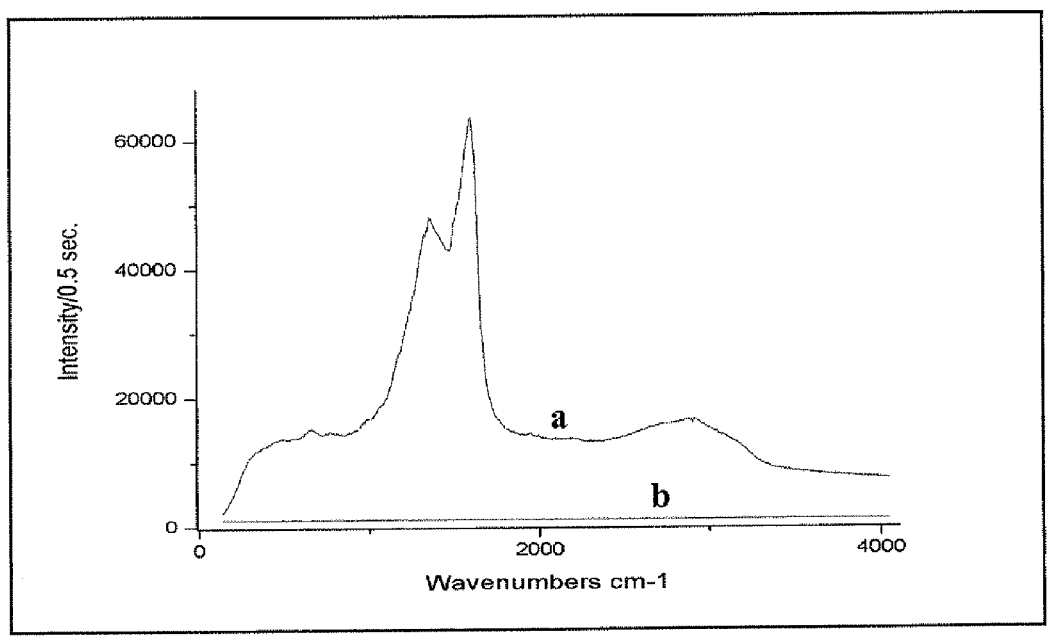
FIG. 5 Raman spectra of ridge and off-ridge portions of a clean fingerprint treated with silver colloid.

When applied to improving the visualization of fingerprint ridges, utilization of SERS offers the advantages of high specificity and high sensitivity, as illustrated in FIGS. 4 and 5. FIG. 4 shows spectra off the ridge (a) and on the ridge (b). FIG. 5 shows spectra for a clean fingerprint treated with silver colloid, for both on ridge (a) and off ridge (b). The spectra acquisition conditions for both were 300 g/mm grating, 0.5 sec exposure time, and laser power of 5 mW at the laser with a 514 argon ion laser. High specificity comes from both the visualizing reagent and the high degree of specificity inherent in Raman spectroscopy. High sensitivity will result from the EM and CT coupling of the fingerprint components to the visualization reagent resulting in SERS enhancement of the measure Raman signal. SERS is just one of several Raman chemical imaging techniques. Other Raman-enhancement methods in addition to SERS are also applicable.

EXAMPLE 11

Raman Chemical Imaging of Fingerprint on SERS Substrate

Figure 6:
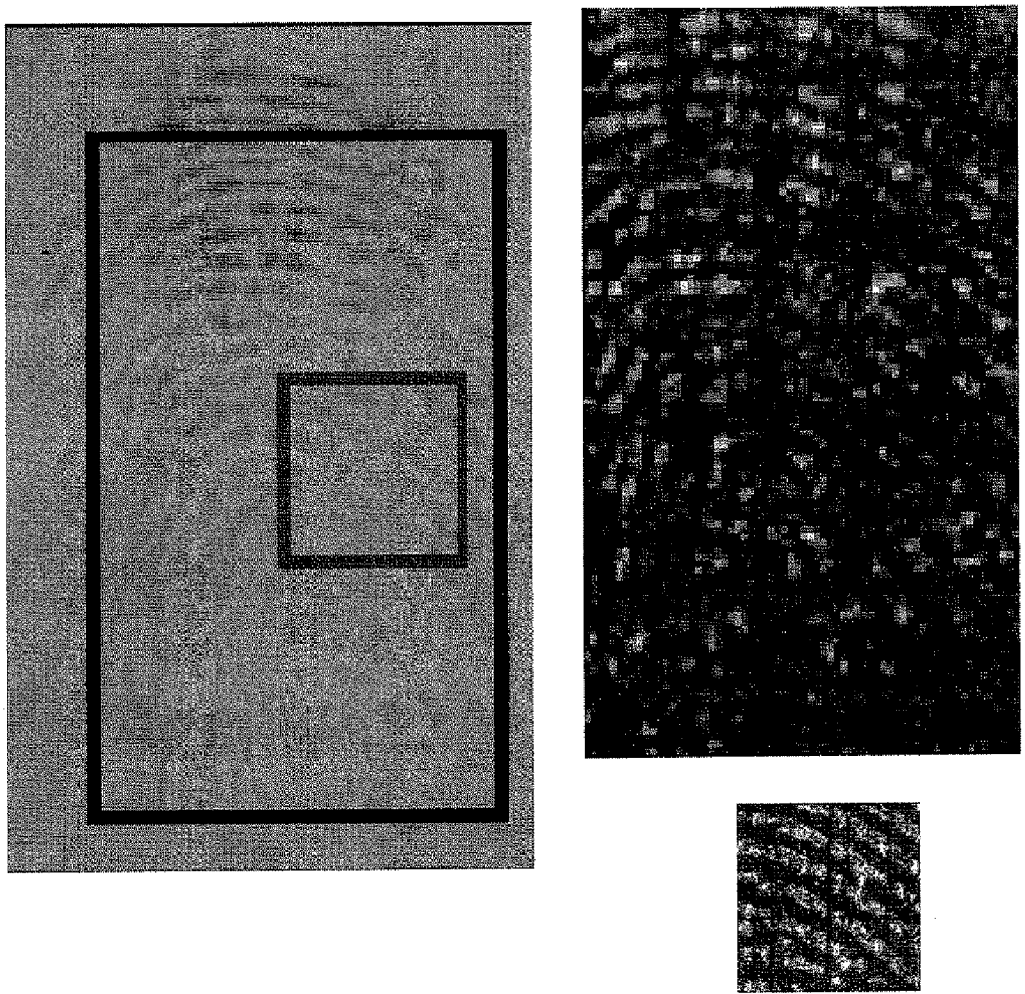
FIG. 6 Raman chemical imaging of a fingerprint on a SERS substrate.

An oily fingerprint (containing both eccrine and sebaceous materials) was placed directly onto a piece of nanocomposite SERS substrate. This Raman-enhancing material was prepared by casting polydimethylsiloxane elastomer onto a flat surface and introducing a Raman-enhancing metal (e.g., silver or gold) to that surface via the process of physical vapor deposition under $10^{-6}$ Torr vacuum. The corresponding Raman spectra are shown in FIG. 6. This result represents the first direct detection of a fingerprint image based on the vibrational scattering signal (Raman) from the chemical components of the fingerprint. The Raman image was collected by illuminating a 1 cm diameter spot on the fingerprint/SERS substrate sample and collecting the scattered light at a number of pertinent shifts in the vibrational spectrum with a chemical imaging spectrometer available from ChemImage, Inc., Pittsburgh, Pa.

EXAMPLE 12

Figure 7:
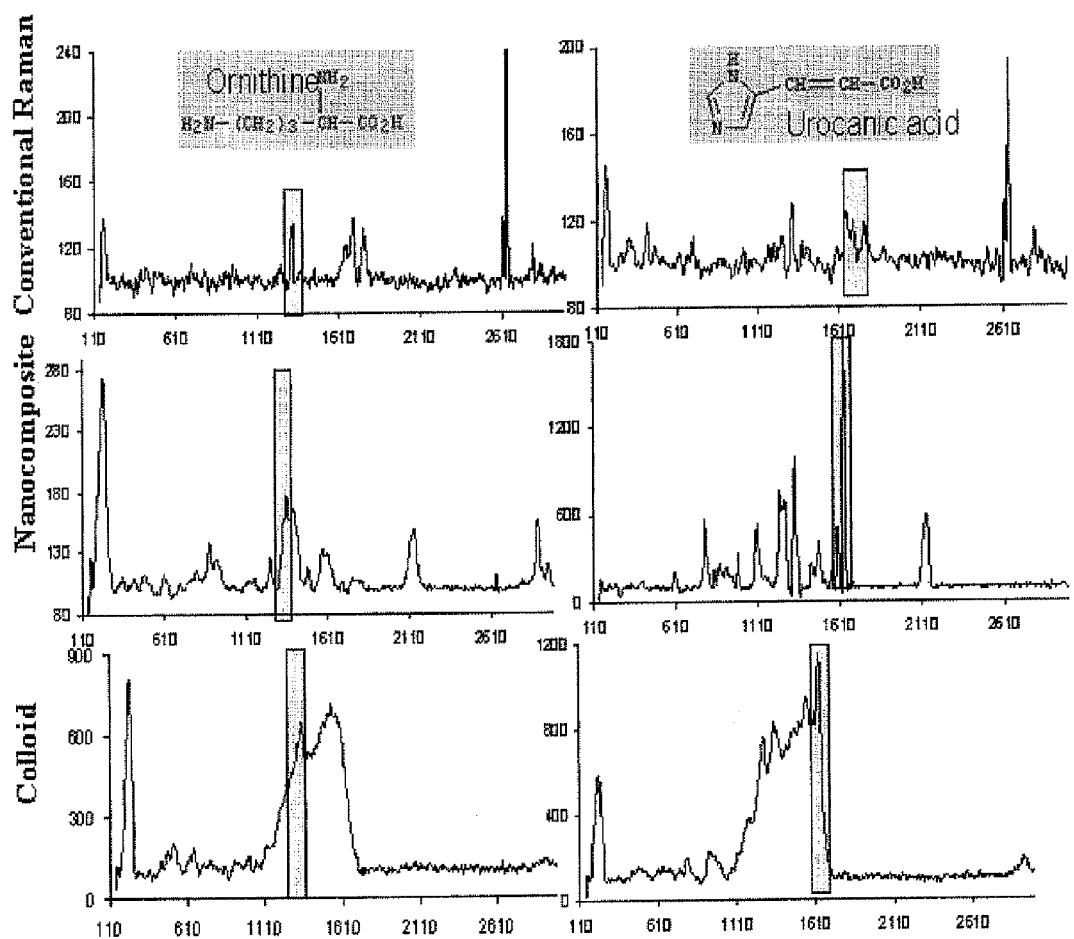
FIG. 7 Comparison of Raman spectral graphs of fingerprint components acquired by conventional Raman and SERS.

Activity of Fingerprint Components Using Conventional Raman, Silver-Elastomer Nanocomposite, and Silver Colloid Substrates Individual chemical components, ornithine and urocanic acid, were evaluated using two different types of surface enhanced Raman materials, as well as collecting conventional Raman spectra of the neat or solid chemicals. Nanocomposite substrate was prepared as described in Example 11. Silver colloid was prepared by reducing aqueous $Ag^+$ with trisodium citrate under heated, stirred conditions. Solutions of the fingerprint components were prepared in water at $10^{-4}$M for colloid testing and $10^{-5}$M for testing on nanocomposite. No conventional Raman spectra were detectable in the $10^{-4}$ M aqueous solutions. The results shown in FIG. 7 illustrate the orders-of-magnitude greater detection sensitivity and lower concentration detection limits achievable by employing surface-enhanced Raman (detects $10^{-5}$M concentrations) relative to conventional Raman (neat or solid samples required to acquire any discernible signal). In addition, these results demonstrate the capabilities of two different types of SERS substrates to elucidate common vibrational bands also present in the conventional Raman spectra arising from fingerprint components. These common bands are highlighted in the small rectangles shown in FIG. 7.

EXAMPLE 13

Spectra from Real Eccrine and Sebaceous Prints on Glass

Figure 8:
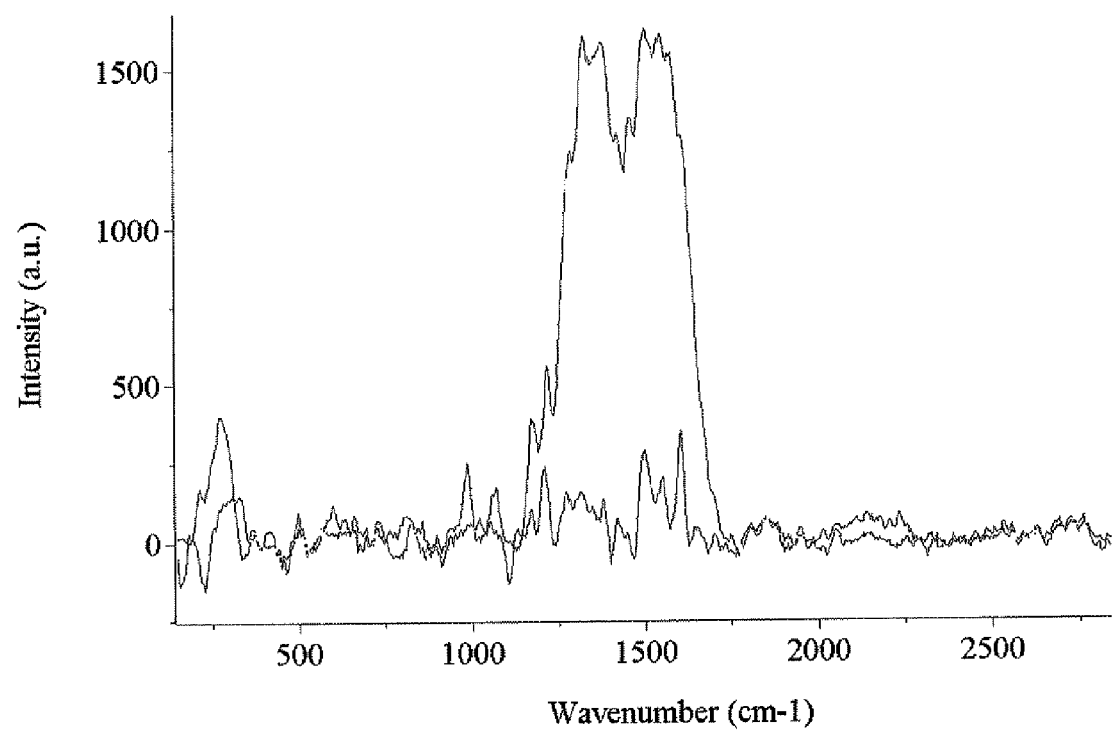
FIG. 8 SERS spectra of real eccrine and sebaceous fingerprints on glass.

The spectra in FIG. 8 show enhancement facilitated by Raman-enhancing silver nanoparticles prepared via aqueous reduction described in Example 12 and deposited with an air-propelled dispersal instrument from a methanol delivery solvent on a two day old latent print on roughened glass. The lower trace is signal from outside the region where the fingerprint was laid down prior to SERS substrate deposition and the top signal trace results where the 633 nm helium-neon laser is used to collect Raman spectra from on one of the print ridges. Notice should be taken of the appearance of both a urea band at ~1100 $cm^{-1}$ (bracketed by the vertical lines) as well as the appearance of a large increase in the region of the spectrum between 1200 $cm^{-1}$ and 1600 $cm^{-1}$, indicative of the detection of both the amino acids and the hydrocarbon character of organic acids or any sebaceous material in the fingerprint. This result is significant in that it demonstrates the power of SERS to distinguish fingerprint from background, even in the case of a latent print found on a rough, and therefore more difficult to image, surface.

EXAMPLE 14

Raman Chemical Imaging of Fingerprint on Aluminum Substrate

Figure 9:
FIG. 9 Raman chemical imaging of fingerprints on an aluminum substrate.

A sebaceous fingerprint was placed on an aluminized slide and imaged by detecting signal from vibrational bands of hydrocarbonaceous oils with a ChemImage, Inc., instrument. In order to better evaluate the Raman response improvement resulting from the SERS active substrate, a set of Raman images was collected from a sebaceous fingerprint on a mirrored aluminum surface, which is known to be non-SERS active. This data is shown in FIG. 9. The distribution of oily hydrocarbonaceous chemicals within the oily print was used to create the image.

While there have been shown and described what are at present considered the preferred embodiments of the invention, it will be obvious to those skilled in the art that various changes and modifications can be prepared therein without departing from the scope of the inventions defined by the appended claims.

What is claimed is:

1. A method for detecting a print on a surface, the method comprising:
    (a) contacting the print with a Raman surface-enhancing agent to produce a Raman-enhanced print; and
    (b) detecting the Raman-enhanced print using a Raman spectroscopic method, wherein said detecting comprises imaging the print by correlating one or more Raman spectral signals emanating from the Raman-enhanced print with one or more chemical components of the print, and determining the distribution of said Raman spectral signals over the surface.

2. The method of claim 1, wherein the Raman surface-enhancing agent is contacted with the print by applying the surface-enhancing agent directly onto the print.

3. The method of claim 1, wherein the Raman surface-enhancing agent is contacted with the print by transferring components of the print to a surface containing the Raman surface-enhancing agent.

4. The method of claim 1, wherein the Raman surface-enhancing agent comprises a zerovalent noble metal.

5. The method of claim 1, wherein the Raman surface-enhancing agent comprises zerovalent gold, silver, or copper nanoparticles.

6. The method of claim 1, wherein the Raman surface-enhancing agent comprises a transition metal oxide.

7. The method of claim 1, wherein the Raman surface-enhancing agent comprises nanorods of zerovalent noble metals or transition metal oxides.

8. The method of claim 1, wherein the Raman surface-enhancing agent comprises silver-containing nanorods.

9. The method of claim 1, wherein the method further comprises identifying one or more chemical components of the print by correlating one or more Raman spectral signals emanating from the Raman-enhanced print with said one or more chemical components.

10. The method of claim 9, wherein the one or more chemical components being identified is a drug, explosive, or firearm residue.

11. The method of claim 1, wherein the print comprises a latent fingerprint.

12. The method of claim 11, wherein a fingerprint pattern is elucidated.

13. The method of claim 12, wherein the fingerprint pattern is elucidated by correlating one or more Raman spectral signals emanating from the Raman-enhanced print with one or more natural components found in finger excretions and determining the distribution of said Raman spectral signals over the surface.

14. The method of claim 13, wherein the one or more natural components comprise amino acids.

15. The method of claim 13, wherein the one or more natural components comprise one or more carboxylic acids.

16. The method of claim 15, wherein the one or more carboxylic acids comprise lactic acid.

17. The method of claim 12, further comprising identifying one or more chemical compounds in the fingerprint.

18. The method of claim 17, wherein the one or more chemical compounds being identified is a drug, explosive, or firearm residue.

19. The method of claim 12, wherein the latent fingerprint is a decomposed latent fingerprint.

20. The method of claim 19, wherein a pattern of the decomposed latent fingerprint is elucidated by correlating one or more Raman spectral signals emanating from the Raman-enhanced print with one or more decomposition products found in decomposed latent fingerprints and determining the distribution of said Raman spectral signals over the surface.

21. The method of claim 12, wherein the latent fingerprint is eccrine in nature.

22. The method of claim 12, wherein the latent fingerprint is sebaceous in nature.

23. The method of claim 12, wherein the latent fingerprint resides on a surface selected from the group consisting of glass, metal, plastic, wood, paper, polymer, and skin.

24. The method of claim 11, wherein the latent fingerprint resides on a skin surface.

25. The method of claim 11, wherein the latent fingerprint resides on a steel surface.

26. The method of claim 11, wherein the latent fingerprint resides on a porous surface.

27. The method of claim 11, wherein the latent fingerprint resides on a rough surface.

28. The method of claim 11, wherein the Raman surface-enhancing agent is contacted with the latent fingerprint by applying the surface-enhancing agent directly onto the latent fingerprint.

29. The method of claim 11, wherein the Raman surface-enhancing agent is contacted with the latent fingerprint by transferring the latent fingerprint to a surface containing the Raman surface-enhancing agent.

30. The method of claim 11, wherein the Raman surface-enhancing agent comprises a zerovalent noble metal.

31. The method of claim 11, wherein the Raman surface-enhancing agent comprises zerovalent gold, silver, or copper nanoparticles.

32. The method of claim 11, wherein the Raman surface-enhancing agent comprises a transition metal oxide.

33. The method of claim 11, wherein the Raman surface-enhancing agent comprises nanorods of zerovalent noble metals or transition metal oxides.

34. The method of claim 11, wherein the Raman surface-enhancing agent comprises zerovalent noble metal-containing nanorods.

35. The method of claim 11, wherein the Raman surface-enhancing agent comprises silver-containing nanorods.

* * * * *